United States Patent [19]

Payne et al.

[11] 4,336,260

[45] Jun. 22, 1982

[54] METHOD AND COMPOSITIONS USING 1-ARYL-1,2,3,4-TETRAHYDRO-β-CARBOLINE-3-CARBOXYLIC ACID FOR TREATING DEPRESSION

[75] Inventors: Alan J. Payne, Noblesville; Michael V. Aylott, Thorntown; Jimmie L. Moore, Indianapolis, all of Ind.; Edward M. Yokley, Cambridge, Mass.

[73] Assignee: The Dow Chemical Company, Midland, Mich.

[21] Appl. No.: 16,757

[22] Filed: Mar. 2, 1979

Related U.S. Application Data

[63] Continuation-in-part of Ser. No. 858,593, Dec. 8, 1977, abandoned.

[51] Int. Cl.$^3$ .................. A61K 31/44; A61K 31/435; A61K 31/455

[52] U.S. Cl. ..................... 424/266; 424/256; 424/263

[58] Field of Search ............... 424/263, 256, 266

[56] References Cited

U.S. PATENT DOCUMENTS 3,459,758  8/1969  Wagner ........................ 424/267

OTHER PUBLICATIONS

Jacobs, J. Biol. Chem., pp. 759–765 (1936).
Snyder, J. Amer. Chem. Soc., pp. 219–220 (1948).

*Primary Examiner*—Stanley J. Friedman
*Attorney, Agent, or Firm*—G. D. Street

[57] ABSTRACT

Treatment of central nervous system depression in a mammal using method and compositions employing 1-aryl-1,2,3,4-tetrahydro-β-carboline-3-carboxylic acids, esters and pharmaceutically-acceptable salts.

32 Claims, No Drawings

METHOD AND COMPOSITIONS USING 1-ARYL-1,2,3,4-TETRAHYDRO-β-CARBOLINE-3-CARBOXYLIC ACID FOR TREATING DEPRESSION

CROSS-REFERENCE TO RELATED APPLICATIONS

This application is a continuation-in-part of copending U.S. patent application Ser. No. 858,593 filed Dec. 8, 1977, now abandoned.

BACKGROUND OF THE INVENTION

The synthesis of various 1-aryl-1,2,3,4-tetrahydro-β-carboline-3-carboxylic acids have been described in the literature. See J. Biol. Chem. 113, 759 (1936) and J. Amer. Chem. Soc. 70, 219 (1948). Other β-carboline derivatives lacking the aryl substitution serve as intermediates in the preparation of compounds having psychoactive properties. See U.S. Pat. Nos. 3,644,384 and 3,717,638. Compounds less closely related in structure have been found to possess central nervous activity. See U.S. Pat. Nos. 3,478,051 and 3,551,450.

SUMMARY OF THE INVENTION

The present invention is directed to a method for treating depression in a mammal and to psychoactive compositions employing a compound of Formula I

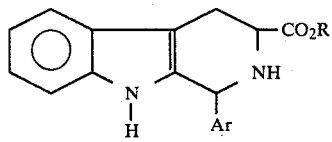

wherein R represents hydrogen or a lower alkyl and Ar represents aryl or substituted aryl. As used herein, aryl includes indanyl, naphthyl, phenyl, and 3,4-(methylenedioxy)phenyl. Moieties suitable for substitution on the aryl group include lower alkyl, lower alkoxy, halo, nitro, amino, monoloweralkylamino, and diloweralkylamino. As used herein both with respect to R and substituted Ar, the terms "loweralkyl" and "lower alkoxy" refer to a moiety having from one to about three carbon atoms.

The invention also includes the pharmaceutically-acceptable salts of the β-carboline carboxylic acids, i.e. where R is hydrogen, used in the practice of the present invention. Pharmaceutically-acceptable salts refer to the acid addition salts of those bases which will form a salt with a carboxylic acid and which will not cause an adverse physiological effect when administered to an animal at dosages consistent with good pharmacological activity. Suitable bases thus include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary, and tertiary amines and the like. Also aluminum salts of the instant compounds may be obtained by treating the corresponding sodium salt with an appropriate aluminum complex such as aluminum chloride hexahydrate, etc.

In general, the compounds of the present invention are effective when administered in daily dosages of from about 0.5 mg to about 80 mg of active ingredient per kilogram of body weight to relieve depression in a mammal. The compounds are administered internally as a psychoactive composition to a mammal either orally or parenterally by subcutaneous, intravenous or intraperitoneal injection or the like, or by implantation or the like, oral administration being preferred. The effective antidepressant amount of the compounds of the invention to be administered internally to a mammal, that is the amount which is effective to substantially relieve a mammal of the symptoms of depression, can vary depending upon such factors as the animal treated, the particular compound administered, the period of administration, and the method of administration.

DETAILED DESCRIPTION OF THE INVENTION

The preparation of 1,2,3,4-tetrahydro-β-carboline-3-carboxylic acids has been described in the literature. See J. Biol. Chem. 113, 759 (1936) and J. Amer. Chem. Soc. 70, 219 (1948). In general, the compounds used in the practice of this invention are prepared by the condensation of l-tryptrophan with a preselected aromatic aldehyde in an acidic aqueous medium. The acids were isolated by making the reaction mixture basic with ammonium hydroxide. Unreacted aldehyde was extracted by washing the mixture with ether. The acid crystallized upon heating the aqueous solution. The acid may be easily converted to the desired ester by treatment with a lower alcohol and an acid, such as, for example, hydrogen chloride.

Compounds corresponding to the general formula

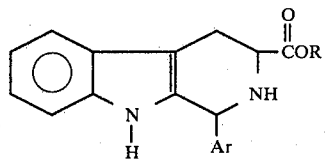

were prepared using the method described above and are listed in Table I below.

TABLE I

| Compound Example No. | Ar = | R = |
| --- | --- | --- |
| 1 | phenyl | H |
| 2 | 4-nitrophenyl | H |
| 3 | 4-(dimethylamino)phenyl | H |
| 4 | 4-methoxyphenyl | H |
| 5 | phenyl | CH$_3$ |
| 6 | 4-nitrophenyl | CH$_3$ |
| 7 | 4-(dimethylamino)phenyl | CH$_3$ |
| 8 | 4-methoxyphenyl | CH$_3$ |
| 9 | 4-methylphenyl | H |
| 10 | 2-naphthyl | H |
| 11 | 5-indanyl | H |
| 12 | 3,4-methylenedioxyphenyl | H |
| 13 | 3,4-dimethoxyphenyl | H |
| 14 | 2-fluorophenyl | H |
| 15 | 3-fluorophenyl | H |
| 16 | 4-fluorophenyl | H |
| 17 | 4-chlorophenyl | H |
| 18 | 4-methylphenyl | CH$_3$ |
| 19 | 2-naphthyl | CH$_3$ |
| 20 | 5-indanyl | CH$_3$ |
| 21 | 3,4-methylenedioxyphenyl | CH$_3$ |
| 22 | 3,4-dimethoxyphenyl | CH$_3$ |
| 23 | 2-fluorophenyl | CH$_3$ |
| 24 | 3-fluorophenyl | CH$_3$ |
| 25 | 4-fluorophenyl | CH$_3$ |
| 26 | 4-chlorophenyl | CH$_3$ |

Compounds wherein R is ethyl or propyl may be prepared using the same general procedure as outlined above.

In practicing the method of the invention, one or more of the compounds of Formula I is administered internally to a mammal by a route effective to introduce an effective antidepressant amount of the compound into the blood stream of the mammal. Administration can be carried out either by a parenteral route such as intravenous, intraperitoneal, subcutaneous or intramuscular injection, or by introduction into the gastrointestinal tract by oral administration, for example, to introduce the compounds into the blood via the gastrointestinal tract. The active acids, esters, or salts are orally effective, and generally have a higher ratio of effective dose to toxic dose when orally administered, and this route is preferred. The effective amount of the active compounds to be administered can also be referred to as an "effective antidepressant amount" (amount sufficient to alleviate Central Nervous System depression).

The effective antidepressant amount of the compound, that is, the amount of the active ingredient sufficient to provide the desired effect depends on various known factors such as the size, type, age and condition of the animal to be treated, the particular acid, ester or pharmaceutically-acceptable salt employed, the route and frequency of administration, the type and degree of Central Nervous System depression involved, the time the compound is administered relative to prior and subsequent presentation of food and liquids, and the like factors. In particular cases, the dosage to be administered can be ascertained by conventional range finding techniques, for example, by observing the effect produced at different dosage rates.

Generally, the compound is preferably administered at a daily dosage rate of from about 0.5 to about 20 mg/kg of bodyweight. Higher dosage rates may be employed, for example, when the compound is administered orally in a timed release dosage form. In the case of mammals suffering from Central Nervous System depression (exhibiting symptoms of depression), administration of an antidepressant amount of the active compound is preferably repeated at predetermined intervals. It is generally desirable to administer the individual dosages at the lowest antidepressant amount which provides the desired continuity consonant with a convenient dosing schedule.

In practicing the method of the invention, the compounds as active ingredient, preferably is incorporated into a composition comprising a pharmaceutical carrier and from about 0.001 to about 95 percent by weight of the compound or a pharmaceutically-acceptable salt thereof. The term "pharmaceutical carrier" refers to known pharmaceutical excipients useful in formulating pharmacologically-active compounds for internal administration to animals, and which are substantially non-toxic and non-sensitizing under conditions of use.

Suitable pharmaceutical carriers are known and disclosed in texts such as Remington's Pharmaceutical Sciences, Thirteenth Ed., Martin (Ed.) Mack Publishing Co., Easton, Pa. (1965). The compositions can be prepared by known techniques for the preparation of tablets, capsules, lozenges, troches, elixirs, syrups, emulsions, dispersions, wettable and effervescent powders, sterile injectable compositions, and can contain suitable excipients known to be useful in the preparation of the particular type of composition desired.

Dosage units adaptable to oral administration such as tablets, capsules, lozenges, elixirs, syrups and the like are preferred and the active compound can be formulated in conventional timed release capsule or tablet formulations. Compositions for oral use include unit dosage forms such as capsules and compressed tablets, containing a pharmaceutical carrier and from about 1 to about 500 milligrams of active compound per unit with from 5 to about 150 milligrams being preferred.

Generally, a syrup dosage unit intended for oral administration most preferably contains from about 5 to about 100 milligrams of the active drug in a pharmaceutically acceptable water soluble salt presented in about 5 milliliters (approximately 1 teaspoon) of a flavored, sweetened hydroalcoholic vehicle. Tablets intended for oral administration generally will contain from about 5 to 500 milligrams of the active drug compressed in a suitable tablet matrix. Another satisfactory dosage unit form would include from about 5 to 250 milligrams of the active drug plus pharmaceutically acceptable excipients filled in a conventional hard gelatin capsule.

Other preferred compositions include sterile injectable solutions containing from about 0.001 to about 10 percent by weight of the active compound in a pharmaceutical carrier suitable for injection, such as isotonic saline solution, Ringer's Injection USP, and lactated Ringer's USP, and the like.

The following examples further illustrate the method that is the present invention.

EXAMPLE 27

Four mice of the same origin and past history were administered 2.5 mg/kg body weight of the compound 1-(4-chlorophenyl)-1,2,3,4-tetrahydro-3-carbomethoxy-$\beta$-carboline (compound Example No. 26) by intraperitoneal injection in an aqueous carrier. Thirty minutes after the administration of the test compound, the mice were administered reserpine at a dosage rate of 2.5 milligrams per kilogram by intraperitoneal injection.

In repeated prior check observations, the administration of 2.5 milligrams per kilogram (mg/kg) of reserpine intraperitoneally to mice has been observed to result in a classical progression of symptoms beginning with a characteristic drooping of the eyelids (ptosis) and later culminating in a generalized depression with decreased spontaneous motor activity and decreased responsiveness to auditory and tactile stimuli. Protection from reserpine-induced depression is indicated by the absence of the characteristic ptosis.

The animals were graded after 45 minutes on the following basis: no ptosis=0, partial ptosis=1, complete ptosis=2. Complete protection against reserpine-induced ptosis gives a value of 0 or 100%. The total value for animals injected with the active compound was found to be 4 indicating the mice were 50% protected against reserpine-induced depression as compared to a group of control mice receiving only carrier.

EXAMPLE 28

It is established in the literature that the ability of a compound to inhibit the uptake of neurotransmittors by the synaptosomes is an indicia of antidepressant activity in mammals. This has lead to the development of a in vitro model which can be used to demonstrate antidepressant activity in a drug. According to this model, a synaptosome preparation is incubated at an appropriate temperature with radioactive neurotransmittor, i.e. norepinephrine or serotonin, and the test compound. Following incubation, the synaptosomes are isolated, and the amount of radioactive neurotransmitter in the synaptosomes is determined by liquid scintillation spectrometry using standard techniques known to the art. See M. J. Kuhar, *Life Sciences* 13, 1623 (1973).

Synaptosomes were prepared from the forebrains of male Sprague-Dawley rats which were homogenized in ten volumes of 0.32 M sucrose (pH 7.0). The homogenate was centrifuged, and the resulting pellet was resuspended in 10% homogenate volume of Krebs-Henseleit buffer (pH 7.4).

A reaction mixture was prepared using Krebs-Henseleit buffer (pH 7.4) containing 0.014% $Ca^{++}$, radioactive neurotransmitter at various predetermined concentrations and 10 μg/ml of the carboline compound. This mixture was preincubated for about 5 minutes at 37° C. after which the reaction was initiated by the addition of 100 μl of the synaptosome preparation. The reaction was allowed to continue for exactly 10 minutes and was terminated by rapid filtration of the mixture. The filters were washed and placed in a liquid scintillation vial with 10 ml of Bray's solution. Radioactivity in the isolated synaptosome material was determined by liquid scintillation spectrometry. Percent uptake was determined by comparing radioactivity taken into the test synaptosome preparation with that of a similarly incubated saline control according to the following equation:

$$\% \text{ uptake} = \frac{A - A'}{B - B'}$$

wherein
A = uptake at 37° C. incubation with test compound
A' = uptake at 0° C. incubation with test compound
B = uptake at 37° C. incubation with test saline
B' = uptake at 0° C. incubation with test saline Values less than 100 in Table II indicate inhibition of neurotransmitter uptake and is indicative of antidepressant activity.

The results are given in Table II.

TABLE II

| Compound Example No. | Neurotransmittor Levels* | |
|---|---|---|
| | Norepinephrine | Serotonin |
| 1 | 45 | 69 |
| 2 | 120 | 89 |
| 3 | 80 | 43 |
| 4 | 99 | 83 |
| 5 | 58 | 97 |
| 6 | 52 | 62 |
| 7 | 45 | 64 |
| 8 | 66 | 76 |
| 9 | 63 | 63 |
| 10 | 72 | 62 |
| 11 | 70 | 62 |
| 12 | 60 | 66 |
| 13 | 75 | 81 |
| 14 | 89 | 97 |
| 15 | 82 | 72 |
| 16 | 82 | 74 |
| 12 | 60 | 66 |
| 13 | 75 | 81 |
| 14 | 89 | 97 |
| 15 | 82 | 72 |
| 16 | 82 | 74 |
| 17 | 83 | 94 |
| 18 | 65 | 56 |
| 19 | 71 | 51 |
| 20 | 67 | 50 |
| 21 | 39 | 51 |
| 22 | 101 | 81 |
| 23 | 92 | 90 |
| 24 | 75 | 77 |

TABLE II-continued

| Compound Example No. | Neurotransmittor Levels* | |
|---|---|---|
| | Norepinephrine | Serotonin |
| 25 | 71 | 76 |
| 26 | 65 | 59 |

*Expressed as % uptake of radioactive neurotransmittor as compared to a saline control.

It will be noticed that all of the compounds inhibited the uptake of either norepinephrine or seratonin. Most of the compounds inhibited both neurotransmittors. The following compounds display very good activity and are particularly preferred for use with the present invention:

1-Phenyl-1,2,3,4-tetrahydro-β-carboline-3-carboxylic acid (Example No. 1);
1-(4-(Dimethylamino)phenyl)-1,2,3,4-tetrahydro-3-carbomethoxy-β-carboline (Example No. 7);
1-(4-Methylphenyl)-1,2,3,4-tetrahydro-3-carbomethoxy-β-carboline (Example No. 18);
1-(2-Naphthyl)-1,2,3,4-tetrahydro-3-carbomethoxy-β-carboline (Example No. 19);
1-(5-Indanyl)-1,2,3,4-tetrahydro-3-carbomethoxy-β-carboline (Example No. 20);
1-(3,4-Methylenedioxyphenyl)-1,2,3,4-tetrahydro-3-carbomethoxy-β-carboline (Example No. 21); and
1-(4-Chlorophenyl)-1,2,3,4-tetrahydro-3-carbomethoxy-β-carboline (Example No. 26).

We claim:

1. A method for treating depression in a mammal exhibiting the symptoms of central nervous system depression which comprises administering internally to the mammal an effective antidepressant amount of a compound having the formula

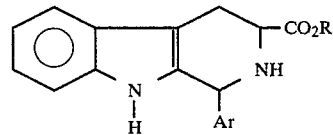

wherein R represents hydrogen or a lower alkyl and Ar represents aryl 3,4-methylenedioxyphenyl or substituted aryl wherein the substituted moiety is a member selected from the group consisting of lower alkyl, lower alkoxy, halo, nitro, amino, monoloweralkylamino, and diloweralkylamino, and further including when R is H the pharmaceutically-acceptable salts of the corresponding acids.

2. The method of claim 1 wherein R represents a lower alkyl.

3. The method of claim 1 wherein R represents hydrogen and further including pharmaceutically-acceptable salts of the acid.

4. The method of claim 1 wherein Ar represents phenyl.

5. The method of claim 1 wherein Ar represents 4-nitrophenyl.

6. The method of claim 1 wherein Ar represents 4-(dimethylamino)phenyl.

7. The method of claim 1 wherein Ar represents 4-methoxyphenyl.

8. The method of claim 1 wherein Ar represents methylphenyl.

9. The method of claim 1 wherein Ar represents 2-naphthyl.

10. The method of claim 1 wherein Ar represents 5-indanyl.

11. The method of claim 1 wherein Ar represents 3,4-methylenedioxyphenyl.

12. The method of claim 1 wherein Ar represents 3,4-dimethoxyphenyl.

13. The method of claim 1 wherein Ar represents 2-fluorophenyl.

14. The method of claim 1 wherein Ar represents 3-fluorophenyl.

15. The method of claim 1 wherein Ar represents 4-fluorophenyl.

16. The method of claim 1 wherein Ar represents 4-chlorophenyl.

17. A composition in dosage unit form comprising a suitable pharmaceutical carrier and from about 1 to about 500 milligrams of a compound having the formula

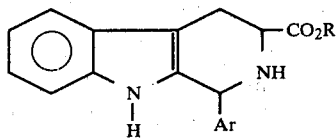

wherein R represents hydrogen or a lower alkyl and Ar represents aryl, 3,4-methylenedioxylphenyl, or substituted aryl wherein the substituted moiety is a member selected from the group consisting of lower alkyl, lower alkoxy, halo, nitro, amino, monoloweralkylamino, and diloweralkylamino, and further including when R is H the pharmaceutically-acceptable salts of the corresponding acids.

18. The composition of claim 17 wherein R represents a lower alkyl.

19. The composition of claim 17 wherein R represents hydrogen and further including pharmaceutically-acceptable salts of the acid.

20. The composition of claim 17 wherein Ar represents phenyl.

21. The composition of claim 17 wherein Ar represents 4-nitrophenyl.

22. The composition of claim 17 wherein Ar represents 4-(dimethylamino)phenyl.

23. The composition of claim 17 wherein Ar represents 4-methoxyphenyl.

24. The composition of claim 17 wherein Ar represents 4-methylphenyl.

25. The composition of claim 17 wherein Ar represents 2-naphthyl.

26. The composition of claim 17 wherein Ar represents 5-indanyl.

27. The composition of claim 17 wherein Ar represents 3,4-methylenedioxyphenyl.

28. The composition of claim 17 wherein Ar represents 3,4-dimethoxyphenyl.

29. The composition of claim 17 wherein Ar represents 2-fluorophenyl.

30. The composition of claim 17 wherein Ar represents 3-fluorophenyl.

31. The composition of claim 17 wherein Ar represents 4-fluorophenyl.

32. The composition of claim 17 wherein Ar represents 4-chlorophenyl.

* * * * *